(12) United States Patent
Balcombe et al.

(10) Patent No.: US 11,986,457 B2
(45) Date of Patent: *May 21, 2024

(54) NUTRACEUTICAL COMPOSITIONS

(71) Applicant: SpecNova LLC, Evergreen, CO (US)

(72) Inventors: Sebastian Balcombe, Evergreen, CO (US); William Hamilton, Cambridge (GB); Jonathan Heal, Cambridge (GB); Joseph Sheridan, Cambridge (GB)

(73) Assignee: SPECNOVA LLC, Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/655,015

(22) Filed: Mar. 16, 2022

(65) Prior Publication Data

US 2022/0296562 A1    Sep. 22, 2022

Related U.S. Application Data

(60) Provisional application No. 63/162,324, filed on Mar. 17, 2021.

(51) Int. Cl.
*A61K 31/353*    (2006.01)
*A61K 45/06*    (2006.01)

(52) U.S. Cl.
CPC ............ *A61K 31/353* (2013.01); *A61K 45/06* (2013.01)

(58) Field of Classification Search
CPC .................................................... A61K 31/353
See application file for complete search history.

(56) References Cited

U.S. PATENT DOCUMENTS

2006/0177409 A1    8/2006    Arnaud

FOREIGN PATENT DOCUMENTS

KR    2011133277    * 12/2011
KR    20110133277 A    12/2011

OTHER PUBLICATIONS

Enzell et al. CAS: 67:21351, 1967.*
Agatharesinol, V.; Enzell, C.R.; Thomas, B.R. Tetrahedron Letters (1966), (22), 2395-402 (Year: 1966).
Chen XH, Kim CS, Kashiwagi T, Tebayashi S, Horiike M. Antifeedants against Acusta despesta from the Japanese cedar, Cryptomeria japonica. Z Naturforsch C J Biosci. Mar.-Apr. 2001;56(3-4):249-52. doi: 10.1515/znc-2001-3-413. PMID: 11371016. (Year: 2001).
Davies, N.T., Wu, HF. & Altaner, C.M. The chemistry and bioactivity of various heartwood extracts from redwood (*Sequoia sempervirens*) against two species of fungi. N.Z. j. of For. Sci. 44, 17 (2014). https://doi.org/10.1186/s40490-014-0017-4 (Year: 2014).
Agatharesinol acetonide, www.thebiotek.com/product/bt-1443289, downloaded Oct. 11, 2023 (Year: 2023).
Zhang, Y.-M., et al., (2005), Chemistry & Biodiversity, 2: 497-505 (Year: 2005).
Liao-Bin Dong, Juan He, Yuan-Yuan Wang, Xing-De Wu, Xu Deng, Zheng-Hong Pan, Gang Xu, Li-Yan Peng, Yu Zhao, Yan Li, Xun Gong, and Qin-Shi Zhao Journal of Natural Products 2011 74 (2), 234-239 DOI: 10.1021/np100694k (Year: 2011).
C.R. Enzell, Y. Hirose, B.R. Thomas, The chemistry of the order araucariales 6. Absolute configurations of agatharesinol hinokiresinol and sugiresinol, Agatharesinol, V.; Tetrahedron Letters 793-798 (Year: 1967).
Balogh, B.; Anderson, A.B. Phytochemistry 1965, 4, 569-575. (Year: 1965).
Hatam et al., J. Chem. Soc. C, 1921-1932 https://pubs.rsc.org/en/content/articlehtml/1969/j3/j39690001921 (Year: 1969).

* cited by examiner

*Primary Examiner* — Rei Tsang Shiao

(74) *Attorney, Agent, or Firm* — Heslin Rothenberg Farley & Mesiti P.C.

(57)    ABSTRACT

The invention relates to nutraceutical compositions comprising dopamine transporter inhibitors and to their use as dietary supplements and food additives.

8 Claims, No Drawings

NUTRACEUTICAL COMPOSITIONS

CROSS REFERENCE TO RELATED APPLICATIONS

This application claims priority to U.S. provisional application No. 63/162,324, filed on Mar. 17, 2021, the entire contents of which are hereby incorporated herein by reference.

FIELD OF THE INVENTION

The invention relates to nutraceutical compositions comprising dopamine transporter inhibitors and to their use as dietary supplements and food additives.

BACKGROUND OF THE INVENTION

The dopamine transporter (also known as the dopamine active transporter, DAT, SLC6A3) is a membrane-spanning protein that pumps the neurotransmitter dopamine out of the synaptic cleft back into cytosol. In the cytosol, other transporters sequester the dopamine into vesicles for storage and later release. Dopamine reuptake via DAT provides the primary mechanism through which dopamine is cleared from synapses, although there may be an exception in the prefrontal cortex, where evidence points to a possibly larger role of the norepinephrine transporter.

The gene that encodes the DAT protein is located on human chromosome 5, consists of 15 coding exons, and is roughly 64 kbp long. Evidence for the associations between DAT and dopamine related disorders has come from a type of genetic polymorphism, known as a VNTR, in the DAT gene (DAT1), which influences the amount of protein expressed.

DAT is implicated in a number of dopamine-related disorders, therefore, there is a need to provide effective dopamine transporter inhibitors.

SUMMARY OF THE INVENTION

According to a first aspect of the invention, there is provided a nutraceutical composition comprising a compound selected from: agatharesinol or a nutraceutically acceptable derivative thereof; or kazinol U; or a nutraceutically acceptable salt or solvate thereof.

DETAILED DESCRIPTION OF THE INVENTION

Dopamine Transporter Inhibitors

According to a first aspect of the invention, there is provided a nutraceutical composition comprising a compound selected from: agatharesinol or a nutraceutically acceptable derivative thereof; or kazinol U; or a nutraceutically acceptable salt or solvate thereof.

In one embodiment, the compound is agatharesinol, or a nutraceutically acceptable salt or solvate thereof.

References herein to "agatharesinol" refer to a compound having the following structure:

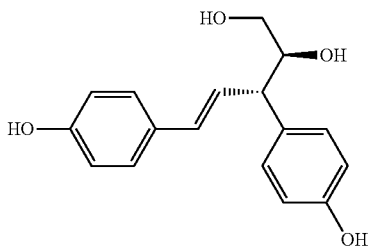 [SMILES: OC[C@@H](O)[C@@H](/C=C/c1ccc(O)cc1)c1ccc(O)cc1]

Agatharesinol (MolPort Number 039-141-773; CAS Number 7288-11-1; PubChem CID 15558522) is known chemically as (2S,3S,4E)-3,5-bis(4-hydroxyphenyl)pent-4-ene-1,2-diol. Agatharesinol is a naturally occurring compound which has been previously characterised as a major heartwood norlignane, however, this compound has neither previously been formulated in a nutraceutical composition nor disclosed for being of potential use as a dietary supplement or food additive. Data is provided herein which shows that agatharesinol demonstrated an extremely high level of inhibition in the dopamine transporter inhibitory assay.

In one embodiment, the compound is agatharesinol, or a nutraceutically acceptable derivative thereof, or a nutraceutically acceptable salt or solvate thereof.

References herein to a "nutraceutically acceptable derivative of agatharesinol" refer to any compound which, upon administration to the recipient, is capable of providing (directly or indirectly) agatharesinol or an active metabolite or residue thereof. In one embodiment, the nutraceutically acceptable derivative of agatharesinol is sequirin C.

References herein to "sequirin C" refer to a compound having the following structure:

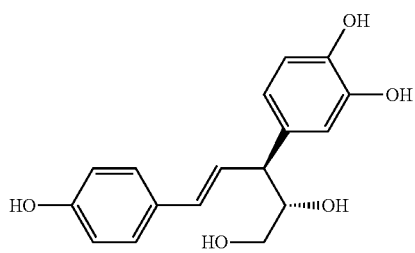 [SMILES: OC[C@@H](O)[C@@H](/C=C/c1ccc(O)cc1)c1ccc(O)c(O)c1]

Sequirin C (MolPort Number 039-338-294; CAS Number 18194-29-1; PubChem CID 12315463) is known chemically as 4-[(1S,2E)-1-[(1S)-1,2-dihydroxyethyl]-3-(4-hydroxyphenyl)prop-2-en-1-yl]benzene-1,2-diol. Sequirin C is a naturally occurring compound which has been previously characterised as a norlignan that is a derivative of agatharesinol in which the second aromatic ring has an additional hydroxy substituent ortho to the one present in the parent compound. It is believed to have a role as a metabolite, however, this compound has neither previously been formulated in a nutraceutical composition nor disclosed for being of potential use as a dietary supplement or food additive. Data is provided herein which shows that sequirin C demonstrated an extremely high level of inhibition in the dopamine transporter inhibitory assay.

According to a further aspect of the invention, there is provided a nutraceutical composition comprising a compound selected from: agatharesinol; or sequirin C; or kazinol U; or a nutraceutically acceptable salt or solvate thereof.

According to a further aspect of the invention, there is provided a nutraceutical composition comprising a compound selected from: agatharesinol; or sequirin C; or a nutraceutically acceptable salt or solvate thereof.

In one embodiment, the compound is kazinol U, or a nutraceutically acceptable salt or solvate thereof.

References herein to "kazinol U" refer to a compound having the following structure:

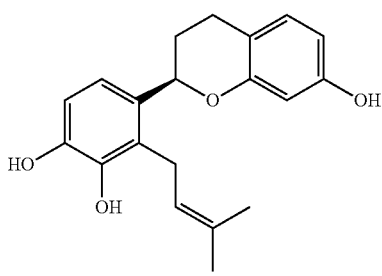 [SMILES: CC(C)=CCc1c([C@H]2CCc3ccc(O)cc3O2)ccc(O)c1O]

Kazinol U (MolPort Number 039-337-109; CAS Number 1238116-48-7; PubChem CID 51136520) is known chemically as 4-[(2S)-7-hydroxy-3,4-dihydro-2H-chromen-2-yl]-3-(3-methylbut-2-enyl)benzene-1,2-diol. Kazinol U is a naturally occurring compound which has been previously characterised as a prenylated flavan isolated from *Broussonetia kazinoki*, however, this compound has neither previously been formulated in a nutraceutical composition nor disclosed for being of potential use as a dietary supplement or food additive. Data is provided herein which shows that kazinol U demonstrated a high level of inhibition in the dopamine transporter inhibitory assay.

References to compounds of the invention also include ionic forms, salts, solvates, isomers (including geometric and stereochemical isomers), tautomers, esters, prodrugs, isotopes and protected forms thereof, for example, as discussed below; preferably, the salts or tautomers or isomers or solvates thereof; and more preferably, the salts or tautomers or solvates thereof, even more preferably the salts or tautomers or solvates thereof. Hereinafter, compounds and their ionic forms, salts, solvates, isomers (including geometric and stereochemical isomers), tautomers, esters, prodrugs, isotopes and protected forms thereof as defined in any aspect of the invention (except intermediate compounds in chemical processes) are referred to as "compounds of the invention".

Salts

Certain compounds of the invention can exist in the form of salts, for example acid addition salts or, in certain cases salts of organic and inorganic bases such as carboxylate, sulfonate and phosphate salts. All such salts are within the scope of this invention, and references to compounds of the invention include the salt forms of the compounds.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002.

Generally, such salts can be prepared by reacting the free acid or base forms of these compounds with the appropriate base or acid in water or in an organic solvent, or in a mixture of the two; generally, non-aqueous media such as ether, ethyl acetate, ethanol, isopropanol, or acetonitrile are used.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, methanesulfonic (mesylate), ethanesulfonic, naphthalenesulfonic, valeric, acetic, propanoic, butanoic, malonic, glucuronic and lactobionic acids. One particular salt is the hydrochloride salt.

The compounds of the invention may exist as mono- or di-salts depending upon the $pK_a$ of the acid from which the salt is formed.

It will be appreciated that for use in medicine the salts of the compounds of the invention should be nutraceutically acceptable. References herein to nutraceutically acceptable should be construed as being equivalent to pharmaceutically acceptable. Suitable pharmaceutically acceptable salts will be apparent to those skilled in the art. Pharmaceutically acceptable salts include those described by Berge, Bighley and Monkhouse, *J. Pharm. Sci.* 1977, 66, pp. 1-19. Such pharmaceutically acceptable salts include acid addition salts formed with inorganic acids e.g. hydrochloric, hydrobromic, sulfuric, nitric or phosphoric acid and organic acids e.g. succinic, maleic, acetic, fumaric, citric, tartaric, benzoic, p-toluenesulfonic, methanesulfonic or naphthalenesulfonic acid. Other salts e.g. oxalates or formates may be used, for example in the isolation of compounds of the invention and are included within the scope of this invention. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Certain of the compounds of the invention may form acid addition salts with one or more equivalents of the acid. The present invention includes within its scope all possible stoichiometric and non-stoichiometric forms.

Solvates

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Pharmaceutically acceptable solvates of the compounds of the invention are within the scope of the invention. In one embodiment, the pharmaceutically acceptable solvates of the compounds of the invention include the hydrate thereof.

Prodrugs

It will be appreciated by those skilled in the art that certain protected derivatives of compounds of the invention, which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". All such prodrugs of compounds of the invention are included within the scope of the invention. Examples of pro-drug functionality suitable for the compounds of the present invention are described in Drugs of Today, 19, 9, 1983, 499-538 and in Topics in Chemistry, Chapter 31, pp. 306-316 and in "Design of Prodrugs" by H. Bundgaard, Elsevier, 1985, Chapter 1. It will further be appreciated by those skilled in the art, that certain moieties, known to those skilled in the art as "pro-moieties", for example as described by H. Bundgaard in "Design of Prodrugs" may be placed on appropriate functionalities when such functionalities are present within compounds of the invention.

Certain specific examples of pro-drugs include sulphonated, glucuronidated, methylated, esterificated, acetylated, glutathionated and glycine conjugated derivatives of the compounds of the invention.

Also included within the scope of the compounds and various salts of the invention are polymorphs thereof.

Enantiomers

Where chiral centres are present in compounds of the invention, the present invention includes within its scope all possible enantiomers and diastereoisomers, including mixtures thereof. The different isomeric forms may be separated or resolved one from the other by conventional methods, or any given isomer may be obtained by conventional synthetic methods or by stereospecific or asymmetric syntheses. The invention also extends to any tautomeric forms or mixtures thereof.

Isotopes

The subject invention also includes all pharmaceutically acceptable isotopically-labelled compounds which are identical to those recited in the compounds of the invention but for the fact that one or more atoms are replaced by an atom having an atomic mass or mass number different from the atomic mass or mass number most commonly found in nature.

Examples of isotopes suitable for inclusion in the compounds of the invention comprise isotopes of hydrogen, such as $^2$H (D) and $^3$H (T), carbon, such as $^{11}$C, $^{13}$C and $^{14}$C, chlorine, such as $^{36}$Cl, fluorine, such as $^{18}$F, iodine, such as $^{123}$I, $^{125}$I and $^{131}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

Certain isotopically-labelled compounds of the invention, for example, those incorporating a radioactive isotope, are useful in drug and/or substrate tissue distribution studies. The compounds of the invention can also have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase) etc. The radioactive isotopes tritium, i.e. $^3$H (T), and carbon-14, i.e. $^{14}$C, are particularly useful for this purpose in view of their ease of incorporation and ready means of detection.

Substitution with heavier isotopes such as deuterium, i.e. $^2$H (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining target occupancy.

Isotopically-labelled compounds of the invention can generally be prepared by conventional techniques known to those skilled in the art using appropriate isotopically-labelled reagents in place of the non-labelled reagent previously employed.

Purity

Since the compounds of the invention are intended for use in nutraceutical compositions it will readily be understood that they are each preferably provided in substantially pure form, for example at least 60% pure, more suitably at least 75% pure and preferably at least 85%, especially at least 98% pure (% are given on a weight for weight basis). Impure preparations of the compounds may be used for preparing the more pure forms used in the nutraceutical compositions.

Processes

It will be apparent that the claimed compounds of the invention are known compounds and may either be purchased commercially or may be prepared in accordance with known procedures.

Nutraceutical Compositions

References herein to a nutraceutical refer to a food, food product, food additive or dietary supplement that provides health and/or medical benefits, such as preventing, treating and enhancing mammalian (e.g. human) conditions. References herein to food extend equally to a drink or beverage comprising said nutraceutical. Thus, according to a further aspect of the invention, there is provided a nutraceutical composition as defined herein, for use as a food, food product, food additive or dietary supplement.

The present invention further provides nutraceutical compositions as defined herein which additionally comprise one or more nutraceutically acceptable excipients.

The present invention further provides nutraceutical compositions, as defined above, and methods of making a nutraceutical composition comprising (e.g admixing) at least one compound of the invention, together with one or more nutraceutical acceptable excipients.

The nutraceutically acceptable excipient(s) can be selected from, for example, carriers (e.g. a solid, liquid or semi-solid carrier), adjuvants, diluents, fillers or bulking agents, granulating agents, coating agents, release-controlling agents, binding agents, disintegrants, lubricating agents, preservatives, antioxidants, buffering agents, suspending agents, thickening agents, flavouring agents, sweeteners, taste masking agents, stabilisers or any other excipients conventionally used in pharmaceutical compositions. Examples of excipients for various types of nutraceutical compositions are set out in more detail below.

The term "nutraceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Nutraceutical compositions containing compounds of the invention can be formulated in accordance with known techniques, see for example, Remington's Pharmaceutical Sciences, Mack Publishing Company, Easton, PA, USA.

The nutraceutical compositions can be administered to the subject in need thereof in any suitable and convenient form. Suitably, said administration will be orally or topically.

Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as sunflower oil, safflower oil, corn oil or olive oil), and injectable organic esters such as ethyl oleate. Proper fluidity can be maintained, for example, by the use of thickening or coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol, sorbic acid, and the like. It may also be desirable to include agents to adjust tonicity such as sugars, sodium chloride, and the like.

Nutraceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures.

Tablets may be designed to release the active compound either upon contact with stomach fluids (immediate release tablets) or to release in a controlled manner (controlled release tablets) over a prolonged period of time or with a specific region of the GI tract.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated. Coatings may act either as a protective film (e.g. a polymer, wax or varnish) or as a mechanism for controlling drug release or for aesthetic or identification purposes. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum, duodenum, jejenum or colon.

Instead of, or in addition to, a coating, the active compound can be presented in a solid matrix comprising a release controlling agent, for example a release delaying agent which may be adapted to release the compound in a controlled manner in the gastrointestinal tract. Alternatively the drug can be presented in a polymer coating e.g. a polymethacrylate polymer coating, which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. In another alternative, the coating can be designed to disintegrate under microbial action in the gut. As a further alternative, the active compound can be formulated in a delivery system that provides osmotic control of the release of the compound. Osmotic release and other delayed release or sustained release formulations (for example formulations based on ion exchange resins) may be prepared in accordance with methods well known to those skilled in the art.

The compounds of the invention may be formulated with a carrier and administered in the form of nanoparticles, the increased surface area of the nanoparticles assisting their absorption. In addition, nanoparticles offer the possibility of direct penetration into the cell. Nanoparticle drug delivery systems are described in "Nanoparticle Technology for Drug Delivery", edited by Ram B Gupta and Uday B. Kompella, Informa Healthcare, ISBN 9781574448573, published 13 Mar. 2006. Nanoparticles for drug delivery are also described in J. Control. Release, 2003, 91 (1-2), 167-172, and in Sinha et al., Mol. Cancer Ther. Aug. 1, (2006) 5, 1909.

The nutraceutical compositions typically comprise from approximately 1% (w/w) to approximately 95% (w/w) active ingredient and from 99% (w/w) to 5% (w/w) of a nutraceutically acceptable excipient or combination of excipients. Particularly, the compositions comprise from approximately 20% (w/w) to approximately 90%,% (w/w) active ingredient and from 80% (w/w) to 10% of a nutraceutically acceptable excipient or combination of excipients. The nutraceutical compositions comprise from approximately 1% to approximately 95%, particularly from approximately 20% to approximately 90%, active ingredient.

The nutraceutically acceptable excipient(s) can be selected according to the desired physical form of the formulation and can, for example, be selected from diluents (e.g solid diluents such as fillers or bulking agents; and liquid diluents such as solvents and co-solvents), disintegrants, buffering agents, lubricants, flow aids, release controlling (e.g. release retarding or delaying polymers or waxes) agents, binders, granulating agents, pigments, plasticizers, antioxidants, preservatives, flavouring agents, taste masking agents, tonicity adjusting agents and coating agents.

The skilled person will have the expertise to select the appropriate amounts of ingredients for use in the formulations. For example tablets and capsules typically contain 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Nutraceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into a polymer or waxy matrix that allow the active ingredients to diffuse or be released in measured amounts.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman, J. Pharm. Sci., 60, 1281-1300 (1971)) and are useful in increasing dissolution rates and increasing the bioavailability of poorly water-soluble drugs.

This invention also provides solid dosage forms comprising the solid solution described above. Solid dosage forms include tablets, capsules, chewable tablets and dispersible or effervescent tablets. Known excipients can be blended with the solid solution to provide the desired dosage form. For example, a capsule can contain the solid solution blended with (a) a disintegrant and a lubricant, or (b) a disintegrant, a lubricant and a surfactant. In addition a capsule can contain a bulking agent, such as lactose or microcrystalline cellulose. A tablet can contain the solid solution blended with at least one disintegrant, a lubricant, a surfactant, a bulking agent and a glidant. A chewable tablet can contain the solid solution blended with a bulking agent, a lubricant, and if desired an additional sweetening agent (such as an artificial sweetener), and suitable flavours. Solid solutions may also be formed by spraying solutions of drug and a suitable polymer onto the surface of inert carriers such as sugar beads ('non-pareils'). These beads can subsequently be filled into capsules or compressed into tablets.

Compositions for topical use and nasal delivery include ointments, creams, sprays, patches, gels, liquid drops and inserts (for example intraocular inserts). Such compositions can be formulated in accordance with known methods.

The compounds of the invention will generally be presented in unit dosage form and, as such, will typically contain sufficient compound to provide a desired level of activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired effect.

Although it is anticipated that the nutraceutical composition of the invention will be present within a tablet or capsule, it may also be within a food or beverage. Examples of suitable foods or beverages where the nutraceutical compositions may be contained within include: water, milk, coffee, tea, juice, protein shake, energy drink, yoghurt, cereal or chocolate bar, and the like.

In one embodiment, the nutraceutical composition additionally comprises one or more additional active ingredients. Suitable additional active ingredients may be those which are also known to provide the same nutraceutical utility as the compounds of the present invention such as those described in US 2015/0132280, US 2018/0055849 and US 2018/0055850, the active agents of which are herein incorporated by reference.

Nutraceutical Utility

It will be appreciated that the nutraceutical composition of the present invention finds utility in any benefit attributed to the dopamine receptor. Thus, according to a further aspect of the invention, there is provided the nutraceutical composition as defined herein, for use in: improving or increasing one or more of the following: mood, self-confidence, relaxation, wakefulness, mental alertness, focus, mental energy, physical energy, natural energy, concentration, reasoning, motivation, stamina, strength, workout output, mobility, athletic speed, reaction time, athletic endurance, alertness, decision making, memory, cognitive performance, verbal fluency, sensuous perception, sexual desire and well being; or reduction of one or more of the following: appetite, boredom, anxiety and fatigue.

The compounds of the present invention may be useful for administration to the adult population. The compounds of the present invention may be useful for administration to the pediatric population.

Biological Data

Human Dopamine Transporter (DAT) Binding (Antagonist Radioligand) Assay

Cell membrane homogenates (20 µg protein) are incubated for 120 min at 4° C. with 4 nM of radiolabelled derivative of the high-affinity dopamine (DA) uptake inhibitor 1-[1-(2-benzo[b]thienyl)cyclohexyl]piperidine [$^3$H] BTCP in the absence or presence of the test compound in a buffer containing 50 mM Tris-HCl (pH 7.4) and 100 mM NaCl. Nonspecific binding is determined in the presence of 10 µM BTCP. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is BTCP, which is tested in each experiment at several concentrations to obtain a competition curve from which its $IC_{50}$ is calculated (Pristupa et al (1994) Mol. Pharmacol. 45, 125).

The compounds of the invention were tested in the above mentioned assay which and the results are shown in the following table:

| Compound | % Inhibition of Control Specific Binding | % of Control Specific Binding (1$^{st}$ Test) | % of Control Specific Binding (2$^{nd}$ Test) | % of Control Specific Binding (mean of two tests) |
|---|---|---|---|---|
| Agatharesinol | 95 | 4.2 | 5 | 4.6 |
| Sequirin C | 94 | 7.4 | 5.6 | 6.5 |
| Kazinol U | 62 | 33.6 | 42.8 | 38.2 |

The invention claimed is:

1. A nutraceutical composition comprising a compound selected from: agatharesinol or a nutraceutically acceptable derivative thereof, wherein the nutraceutically acceptable derivative of agatharesinol is sequirin C; or a nutraceutically acceptable salt or solvate thereof.

2. The nutraceutical composition according to claim 1, wherein the compound is agatharesinol, or a nutraceutically acceptable salt or solvate thereof.

3. The nutraceutical composition according to claim 1, which additionally comprises one or more nutraceutically acceptable excipients.

4. The nutraceutical composition according to claim 1, which additionally comprises one or more additional active ingredients.

5. The nutraceutical composition according to claim 1, which is a tablet or capsule.

6. The nutraceutical composition according to claim 1, which is a food or beverage selected from: water, milk, coffee, tea, juice, protein shake, energy drink, yoghurt and cereal or chocolate bar.

7. A food, food product, food additive or dietary supplement comprising the nutraceutical composition according to claim 1.

8. A method for: improving or increasing one or more of the following: mood, self-confidence, relaxation, wakefulness, mental alertness, focus, mental energy, physical energy, natural energy, concentration, reasoning, motivation, stamina, strength, workout output, mobility, athletic speed, reaction time, athletic endurance, alertness, decision making, memory, cognitive performance, verbal fluency, sensuous perception, sexual desire and/or well being; or reduction of one or more of the following: appetite, boredom, anxiety and/or fatigue; said method comprising administering to a subject the nutraceutical composition according to claim 1.

* * * * *